United States Patent [19]

Lesher et al.

[11] 4,109,092
[45] Aug. 22, 1978

[54] PREPARATION OF 2-(PYRIDINYL)-4-PYRIMIDINAMINES

[75] Inventors: George Y. Lesher, Schodack; Baldev Singh, East Greenbush, both of N.Y.

[73] Assignee: Sterling Drug Inc., New York, N.Y.

[21] Appl. No.: 730,379

[22] Filed: Oct. 7, 1976

[51] Int. Cl.² .......................................... C07D 401/04
[52] U.S. Cl. ........................................................ 544/328
[58] Field of Search ............................... 260/256.4 N

[56] References Cited

PUBLICATIONS

Tsurushima, "Chemical Abstracts", vol. 74, 1971, col. 13174n.
"Chemical Abstracts", vol. 72, 1970, col. 90504f.

Primary Examiner—Donald G. Daus
Assistant Examiner—James H. Turnipseed
Attorney, Agent, or Firm—Robert K. Bair; B. Woodrow Wyatt

[57] ABSTRACT

The process of reacting a PY-carboxamidine with α-chloroacrylonitrile in the presence of an acid-acceptor to produce 2-PY-4-pyrimidinamines where PY is 4- or 3- or 2-pyridinyl or 4- or 3- or 2-pyridinyl having one or two lower-alkyl substituents. The products produced by the process are useful as anti-allergic agents per se and, also, are useful as intermediates in the preparation of other anti-allergic agents, namely, dialkyl N-(2-PY-4-pyrimidinyl)-aminomethylenemalonates and analogs, as well as N-(2-PY-4-pyrimidinyl)ureas.

8 Claims, No Drawings

PREPARATION OF 2-(PYRIDINYL)-4-PYRIMIDINAMINES

CROSS-REFERENCE TO RELATED APPLICATIONS

The products of the instant process are disclosed and claimed in copending application Ser. No. 708,195, filed July 23, 1976, now U.S. Pat. No. 4,032,523 wherein they are shown to be useful not only as anti-allergic agents but also to be useful as intermediates in the preparation of other anti-allergic agents. Copending application Ser. No. 555,067, filed Mar. 3, 1975, now U.S. Pat. No. 4,018,770, issued Apr. 19, 1977, shows the use of the products of the instantly claimed process as intermediates in the preparation of dialkyl N-[2-(pyridinyl)-4-pyrimidinyl]-aminomethylenemalonates and analogs and copending application Ser. No. 556,213, filed Mar. 7, 1975, now U.S. Pat. No. 4,008,235, issued Feb. 15, 1977, shows the use of the products of the instantly claimed process as intermediates in the preparation of N-[2-(pyridinyl)-4-pyrimidinyl]ureas.

BACKGROUND OF THE INVENTION (a) Field of the Invention

This invention relates to a new approach to the synthesis of 2-(pyridinyl)-4-pyrimidinamines utilizing readily available starting materials.

Of the many types of known syntheses of pyrimidines [Chapters II, III and IX of D. J. Brown's text entitled "The Pyrimidines", Interscience Publishers, a Division of John Wiley & Sons, New York, London; also the same chapters of Brown's "The Pyrimidines, Supplement I", 1970, same publisher], none utilize α-chloroacrylonitrile and none result directly in the formation of a 2-substituted-4-pyrimidinamine bearing no other ring substituent.

Ruhemann et al. [Chem. Ber. 30, 2022 (1897)] prepared 2-phenyl-4-pyrimidinamine by reacting 4-chloro-2-phenylpyrimidine with ammonia. The 4-chloro-2-phenylpyrimidine had been prepared in two steps by first reacting benzamidine with sodium formylacetate to produce 2-phenyl-4-pyrimidone and then reacting the latter with phosphorus oxychloride.

Gabriel [Chem. Ber. 37, 3638 (1904)] prepared 2-methyl-4-pyrimidinamine by the same sequence of reactions used by Ruhemann et al., supra, starting with acetamidine in place of benzamidine.

Lardenois et al. [Bull. Soc. Chim. France 1971, (1858)] reported on the results of a tautomeric study of various pyrimidine compounds including 2-phenyl-4-pyrimidinamine and 2-methyl-4-pyrimidinamine. In the beginning of the paper under "methods of syntheses" Lardenois et al. report that the seventy year old synthetic methods of Ruhemann et al. and Gabriel were used respectively to prepare said 2-phenyl-4-pyrimidinamine and 2-methyl-4-pyrimidinamine.

Ege and Arnold [Angew. Chem. internat. Edit. 13, 206 (1974)] recently reported the one step preparation of 3(5)-aminopyrazole by reacting hydrazine hydrate with α-chloroacrylonitrile in alkaline solution (aqueous potassium carbonate). Heretofore, 3(5)-aminopyrazole had been obtainable only by way of multi-step syntheses.

SUMMARY OF THE INVENTION

The invention relates to the process of preparing 2-(pyridinyl)-4-pyrimidinamines by reacting a pyridine-carboxamidine with α-chloroacrylonitrile in the presence of an acid-acceptor.

DETAILED DESCRIPTION INCLUSIVE OF PREFERRED EMBODIMENTS

The invention resides in the process which comprises reacting PY-carboxamidine with α-chloroacrylonitrile in the presence of an acid-acceptor to produce 2-PY-4-pyrimidinamine having Formula I

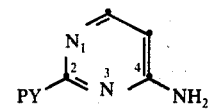

where PY is 4- or 3- or 2-pyridinyl or 4- or 3- or 2-pyridinyl having one or two lower-alkyl substituents. In preferred embodiments, PY is 4-pyridinyl or 3-pyridinyl and the acid-acceptor is an alkali lower-alkoxide, preferably sodium methoxide, The resulting 2-PY-4-pyrimidinamines (I) are useful as anti-allergic agents (claimed in copending application Ser. No. 708,195, filed July 23, 1976) and as intermediates both in the preparation of dialkyl N-(2-PY-4-pyrimidinyl)aminomethylenemalonates and analogs (claimed in copending application Ser. No. 555,067, filed Mar. 3, 1975) and in the preparation of N-(2-PY-4-pyrimidinyl)ureas (claimed in copending application Ser. No. 556,213, filed Mar. 7, 1975).

The term "lower-alkyl" as used herein, e.g., as a substituent for the pyridinyl radical designated as PY, means alkyl radicals having from one to six carbon atoms which can be arranged as straight or branched chains, illustrated by methyl, ethyl, n-propyl, isopropyl, n-butyl, sec.-butyl, tert.-butyl, isobutyl, n-amyl, n-hexyl, and the like.

The compounds of Formula I are useful both in the free base form and in the form of their acid-addition salts. Use of the salt form inherently amounts to use of the base form. The acids which can be used to prepare the acid-addition salts include preferably those which produce, when combined with the free base, medicinally acceptable salts, that is, salts whose anions are relatively innocuous to the animal organism in medicinal doses of the salts, so that the beneficial antiallergic properties inherent in the free base are not vitiated by side affects ascribable to the anions. It was found convenient to form the hydrochloride or methanesulfonate salt. However, other appropriate medicinally acceptable salts are those derived from mineral acids such as phosphoric acid, sulfamic acid, and sulfuric acid; and organic acids such as acetic acid, citric acid, tartaric acid, lactic acid, ethanesulfonic acid, benzenesulfonic acid, p-toluenesulfonic acid, cyclohexylsulfamic acid, quinic acid, and the like, giving the phosphate, sulfamate, sulfate, acetate, citrate, tartrate, lactate, ethanesulfonate, benzenesulfonate, p-toluenesulfonate, cyclohexylsulfamate and quinate, respectively.

The acid-addition salts of said basic compounds are prepared either by dissolving the free base in aqueous or aqueous-alcohol solution containing the appropriate acid and isolating the salt by evaporating the solution, or by reacting the free base and acid in an organic solvent, in which case the salt separates directly or can be obtained by concentration of the solution.

The molecular structures of the products (I) produced by the process of the invention were assigned on the basis of evidence provided by infrared, ultraviolet, nuclear magnetic resonance and mass spectra, by chromatographic mobilities, and, by the correspondence of calculated and found values for the elementary analyses for representative examples.

The manner of making and using the instant invention will now be generally described so as to enable a person skilled in the art of chemistry to make and use the same, as follows:

The process of the invention is carried out by mixing a pyridinecarboxamidine of the formula PY-C(NH)NH$_2$ with α-chloroacrylonitrile in the presence of an acid-acceptor, preferably an alkali lower-alkoxide, particularly sodium methoxide, to produce 2-PY-4-pyrimidinamine, where PY is defined as hereinabove for formula I. The reaction is run preferably in a non-aqueous solvent, most preferably in a lower-alkanol, in particular, methanol, at the temperature range of about 25° to 80° C., preferably about 35° to 50° C. Other solvents include other lower-alkanols, e.g., methanol, n-propanol, isopropyl alcohol, n-butanol, isobutyl alcohol and the like, tetrahydrofuran, dimethylformamide, dioxane, and the like. Other acid-acceptors include other alkali lower-alkoxides, e.g., potassium methoxide, sodium ethoxide, sodium isopropoxide, sodium n-propoxide, potassium n-butoxide, sodium isobutoxide, and the like, alkali hydroxides, e.g., sodium hydroxide, potassium hydroxide. Since the intermediate pyridinamidines are conveniently prepared in the form of their acid-addition salts, e.g., hydrochlorides, the process of the invention is conveniently carried out using the pyridineamidine reactant in the form of its acid-addition salt, preferably hydrochloride, and also using at least two molar equivalents of acid-acceptor per mole of pyridinamidine acid-addition salt, one molar equivalent of acid-acceptor to convert the pyridinamidine to its free base form and the other to participate in the process of the invention. A preferred embodiment of the process of the invention is given below in Example 5.

The following examples will further illustrate the invention without, however, limiting it thereto.

1. 2-(4-Pyridinyl)-4-pyrimidinamine - A mixture containing 31.6 g. of isonicotinamidine hydrochloride, 10.8 g. of sodium methoxide and 100 ml. of methanol was stirred for twenty-five minutes and then evaporated to dryness to give a white residue. To the residue was added 200 ml. of tetrahydrofuran and the mixture stirred. To the stirred mixture was added dropwise over a period of 25 minutes 18 g. of 60 -chloroacrylonitrile whereupon the temperature rose to 45° C. When the temperature started to fall, another 10.8 g. portion of sodium methoxide was added and the resulting mixture was refluxed with stirring for two hours, concentrated in vacuo and diluted with water. The insoluble product was collected and dried in vacuo overnight at 80° C. to yield 21.1 g. of 2-(4-pyridinyl)-4-pyrimidinamine, m.p. 262–263° C.

2. 2-(4-Pyridinyl)-4-pyrimidinamine - A mixture containing 5.4 g. of sodium methoxide, 50 ml. of methanol and 31.6 g. of isonicotinamidine hydrochloride was stirred for thirty minutes and stripped to dryness to remove the solid. To the residue was added 250 ml. of tetrahydrofuran and the resulting slurry was stirred in an ice bath. To the stirred mixture was added dropwise over a period of thirty minutes 18 g. of α-chloroacrylonitrile. After the reaction mixture had been stirred for an additional two hours, it was allowed to stand at room temperature for one hour and then refluxed for four hours. To the reaction mixture was added 15 ml. of 35% aqueous sodium hydroxide solution and the mixture chilled. The solid was collected, washed with water and dried to yield 21.1 g. of 2-(4-pyridinyl)-4-pyrimidinamine, m.p. 264°–267° C.

3. 2-(4-Pyridinyl)-4-pyrimidinamine - A mixture containing 31.6 g. of isonicotinamidine hydrochloride, 10.8 g. of sodium methoxide and 200 ml. of ethanol was stirred at ambient temperature for 30 minutes and then cooled in a running water bath. To the stirred mixture was added 18 g. of α-chloroacrylonitrile dropwise over a period of 25 minutes whereupon the internal temperature arose to 45° C. The reaction mixture was stirred for thirty minutes and then refluxed for two hours. To the reaction mixture was added 13 ml. of 35% aqueous sodium hydroxide solution and the mixture was cooled. The solid was collected, washed successively with water and ethanol and dried to yield 16.8 g. of 2-(4-pyridinyl)-4-pyrimidinamine, m.p. 261°–263° C.

4. 2-(4-Pyridinyl)-4-pyrimidinamine - To an ice cold stirred solution containing 8 g. of sodium hydroxide and 300 ml. of methanol was added 31.6 g. of isonicotinamidine hydrochloride whereupon the temperature of the reaction mixture dropped to 0° C. To the stirred mixture was added dropwise over a period of 30 minutes 18 g. of α-chloroacrylonitrile and the reaction mixture was refluxed for five hours. The methanol was removed in vacuo and to the residue was added water and the mixture slurried. The solid was collected, washed with water and dried in vacuo to yield 12.6. g. of 2-(4-pyridinyl)-4-pyrimidinamine, m.p. 265°–267° C.

5. 2-(4-Pyridinyl)-4-pyrimidinamine - A mixture containing 15.8 g. of isonicotinamidine hydrochloride, 75 ml. of methanol and 5.4 g. of sodium methoxide was stirred for twenty minutes to liberate in solution isonicotinamide in free base form and then 8.9 g. of α-chloroacrylonitrile was added dropwise over a period of fifteen minutes. This was followed by the addition of a solution of 5.4 g. of sodium methoxide and 25 ml. of methanol over a period of forty minutes. The resulting reaction mixture was stirred for an additional three hours, the methanol was distilled-off in vacuo and the residue was diluted with water. The solid was separated, washed successively with water and ethanol and dried to yield 12.1 g. of 2-(4-pyridinyl)-4-pyrimidinamine, m.p. 263°–266° C. A mixed melting point with a sample of 2-(4-pyridinyl)-4-pyrimidinamine prepared by reacting isonicotinamidine with β-ethoxyacrylonitrile and melting at 262°–265° C. (Example A-1 of said copending application Ser. No. 555,067, filed Mar. 3, 1975) shows no depression.

6. 2-(3-Pyridinyl)-4-pyrimidinamine - A mixture containing 5.4 g. of sodium methoxide, 75 ml. of methanol and 15.5 g. of nicotinamidine hydrochloride was stirred for five minutes and then evaporated to dryness to remove the methanol. To the residue was added 75 ml. of tetrahydrofuran and the mixture was stirred. To the stirred mixture was added 8.8 g. of α-chloroacrylonitrile over a period of ten minutes and the resulting reaction mixture was allowed to stir for thirty minutes. There was then added to the stirred mixture a solution containing 4 g. of sodium hydroxide and 7 ml. of water over a thirty minute period and the resulting mixture was stirred for three hours. The tetrahydrofuran was distilled off in vacuo and the residue was diluted with water. The oily product was extracted with chloroform and the chloroform extract was evaporated in vacuo to remove the solvent and to leave 12.6 g. of gummy solid.

The gummy solid was dissolved in 90:10 (v:v) ether methanol and the resulting solution was filtered through 300 g. of silica gel in a 500 ml. Buchner funnel and the silica gel was eluted with 95:5 (v:v) of ether/methanol. The various fractions were evaporated in vacuo to remove the solvent and the fractions containing the desired compound were combined and recrystallized from isopropyl alcohol-ether to yield 6.9 g. of 2-(3-pyridinyl)-4-pyrimidinamine, m.p. 159°–161° C. A mixed melting point with a sample of the same compound, m.p. 157°–159° C., prepared by a different method [by reaction of nicotinamidine with β-ethoxyacrylonitrile (example A-2, copending U.S. application Ser. No. 555,067, filed Mar. 3, 1975)] showed no depression.

7. 2-(2-Pyridinyl)-4-pyrimidinamine - A mixture containing 15.8 g. of picolinamidine hydrochloride, 5.4 g. of sodium methoxide and 75 ml. of methanol was stirred for 10 minutes and then 8.9 g. of α-chloroacrylonitrile was added over a period of 15 minutes followed by the addition of a solution of 5.4 g. of sodium methoxide in 25 ml. of methanol over a period of 35 minutes. The reaction mixture was stirred further for three hours; the insoluble inorganic solid was filtered off; and, the filtrate was concentrated in vacuo to remove the solvent. The residue was dissolved in 100 ml. of boiling ethanol and treated with 8 ml. of methanesulfonic acid; the hot solution was treated with decolorizing charcoal and filtered; and, the filtrate was concentrated and chilled in an ice bath. The separated solid was collected and dried in vacuo at 80° C. overnight to produce 6.1 g. of 2-(2-pyridinyl)-4-pyrimidinamine dimethanesulfonate, m.p. 182°–184° C. This compound was found to have an identical nuclear magnetic resonance spectrum with that of the same compound (m.p. 184°–186° C.) prepared by reacting picolinamidine with β-ethoxyacrylonitrile (Example A-9, copending application Ser. No. 555,067, filed Mar. 3, 1975).

Following the procedure described in Example 5 but using in place of isonicotinamidine a molar equivalent quantity of the appropriate pyridinecarboxamidine, i.e., PY-C(=NH)NH$_2$, the 2-PY-4-pyrimidinamines of Examples 8 thru 11 are obtained:

8. 2-(2-Methyl-4-pyridinyl)-4-pyrimidinamine using 2-methylisonicotinamidine.

9. 2-(3-Methyl-4-pyridinyl)-4-pyrimidinamine using 3-methylisonicotinamidine.

10. 2-(2-Ethyl-4-pyridinyl)-4-pyrimidinamine using 2-ethylisonicotinamidine.

11. 2-(2,6-Dimethyl-4-pyridinyl)-4-pyrimidinamine using 2,6-dimethylisonicotinamidine.

The anti-allergic activity of the compounds of Formula I is determined by showing their effectiveness as inhibitors of release of mediators of allergic reactions by the IgE-mediated passive cutaneous anaphylaxis (PCA) method described as follows (IgE is the abbreviation for Immunoglobulin E, the cell-sensitizing antibody): Sprague-Dawley rats weighing 70 to 90 grams each are injected intradermally with multiple serial dilutions of IgE forty-eight hours before administration of the drug. The rats are fasted overnight (approximately seventeen hours) before the drug administration. Each drug being tested is administered orally at 100 mg./kg. to each of four rats. Six other rats are observed as a control group. One hour after drug administration, 10 mg./kg. of egg albumen was administered intravenously together with 17 mg./kg. of Evans Blue. Thirty minutes later, the rats are killed by cervical fracture, the i.d. injected skin is everted, and the average of two perpendicular diameters of each blue area is recorded. The average diameters vs. the reciprocal of the dilution of antibody in the control group is plotted on a semilog graph, and a best-fitting line is drawn through points for the control rats, and a best-fitting parallel line to the control line is drawn for each tested drug. Comparative drug activity is evaluated by the degree of the shift to the right from controls, that is, by the ratio, R, of:

$$\frac{\text{reciprocal of antibody dilution necessary for zero mm. diameter in control group}}{\text{reciprocal of antibody dilution necessary for zero mm. diameter in medicated group}}.$$

The results are interpreted as follows:

| R (= degree of shift to the right) | Interpretation of Drug Activity |
|---|---|
| 1.0 – 2.0 | Inactive |
| 2 – 4 | Weak |
| 2 – 8 | Moderate |
| >8 | Strong |

When tested by the above procedure, said compounds of formula I were found to have R values > 2, the more active and preferred compounds having R values > 8.

The actual determination of the numerical anti-allergic data definitive for a particular compound produced by the process of the invention is readily obtained according to the above-described standard test procedures by technicians versed in pharmacological test procedures, without any need for any extensive experimentation.

The compounds of Formula I can be prepared I for use by dissolving under sterile conditions a salt form of the compounds in water (or an equivalent amount of a nontoxic acid if the free base is used), or in a physiologically compatible aqueous medium such as saline, and stored in ampules for intramuscular injection. Alternatively, they can be incorporated in unit dosage form as tablets or capsules for oral administration either alone or in combination with suitable adjuvants such as calcium carbonate, starch, lactose, talc, magnesium stearate, gum acacia, and the like. Also, the compounds can be formulated for oral administration in aqueous alcohol, glycol or oil solutions or oil-water emulsions in the same manner as conventional medicinal substances are prepared.

We claim:

1. The process which comprises reacting PY-carboxamidine with α-chloroacrylonitrile in the presence of an acid-acceptor to produce 2-PY-4-pyrimidinamine where PY is 4- or 3- or 2-pyridinyl or 4- or 3- or 2-pyridinyl having one or two lower-alkyl substituents.

2. The process according to claim 1 where PY is 4-pyridinyl.

3. The process according to claim 1 where PY is 3-pyridinyl.

4. The process according to claim 1 where the acid-acceptor is an alkali lower-alkoxide.

5. The process according to claim 1 where PY is 4-pyridinyl and the acid-acceptor is sodium methoxide.

6. The process according to claim 1 where PY is 3-pyridinyl and the acid-acceptor is sodium methoxide.

7. The process according to claim 1 wherein the reaction is carried out between about 25° to 80° C.

8. The process according to claim 1 wherein the reaction is carried out between 35° to 50° C.

* * * * *

UNITED STATES PATENT AND TRADEMARK OFFICE
CERTIFICATE OF CORRECTION

PATENT NO. : 4,109,092
DATED : August 22, 1978
INVENTOR(S) : George Y. Lesher and Baldev Singh It is certified that error appears in the above-identified patent and that said Letters Patent are hereby corrected as shown below:

Column 1, line 31, "The Pyrimidines", Interscience" should read -- "The Pyrimidines", 1962, Interscience --.

Column 2, line 21, "methoxide," should read -- methoxide. --.

Column 3, line 12, "C(NH)NH$_2$" should read -- C(=NH)NH$_2$ --.

Column 3, line 49, "60-chloroacrylonitrile" should read -- α-chloroacrylonitrile --.

Column 3, line 56, "21.1 g." should read -- 21.2 g. --.

Column 6, line 33, "can be prepared I for use" should read -- can be prepared for use --.

Signed and Sealed this

Nineteenth Day of August 1980

[SEAL]

Attest:

SIDNEY A. DIAMOND

Attesting Officer

Commissioner of Patents and Trademarks